US006583270B2

(12) United States Patent
Rosen et al.

(10) Patent No.: US 6,583,270 B2
(45) Date of Patent: Jun. 24, 2003

(54) INTERLEUKIN-19

(75) Inventors: Craig A. Rosen, Laytonsville, MD (US); Joseph J. Kenny, Frederick, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/386,380

(22) Filed: Aug. 31, 1999

(65) Prior Publication Data

US 2002/0032311 A1 Mar. 14, 2002

Related U.S. Application Data

(62) Division of application No. 08/921,382, filed on Aug. 29, 1997, now Pat. No. 5,985,614.
(60) Provisional application No. 60/024,882, filed on Aug. 30, 1996.

(51) Int. Cl.$^7$ .......................... C07K 14/54; C12N 5/10; C12N 15/24; C12N 15/63

(52) U.S. Cl. ................... 530/351; 536/23.5; 435/69.52; 435/71.1; 435/71.2; 435/325; 435/320.1; 435/471; 435/252.3; 435/254.11; 424/85.2

(58) Field of Search .......................... 530/351; 536/23.1, 536/23.5; 435/69.52, 71.2, 320.1, 325, 252.3, 471, 71.1, 254.11; 424/85.2

(56) References Cited

U.S. PATENT DOCUMENTS

| | | | |
|---|---|---|---|
| 5,223,408 A | 6/1993 | Goeddel et al. | ............ 435/69.3 |
| 5,985,614 A | 11/1999 | Rosen et al. | ............. 435/69.52 |

OTHER PUBLICATIONS

Mikayama et al. Proc. Natl. Acad. Sci. USA vol. 90, pp. 10056–10060, 1993.*
Voet. et al. Biochemistry. John Wiley & Sons, Inc., pp. 126–128 and 228–234, 1990.*
Harlow et al. Antibodies A Laboratory Manual. Cold Spring Harbor Laboratory, Chp. 5, p. 76, 1993.*
Hellyer et al. Gene. vol. 165, pp. 279–284, 1995.*
NCBI Entrez, GenBank Report, Accession No. M59456, from Maridor, G., et al. (1993).
NCBI Entrez, GenBank Report, Accession No. U16720, from Sanjanwala, B., and de Waal–Malefyt, R. (Oct. 1995).
Baer, R. et al., "DNA sequence and expression of the B95–8 Epstein–Barr virus genome," Nature 310:207–211 (1984).
Benjamin, D. et al., "Human B–Cell Interleukin–10: B–Cell Lines Derived From Patients With Acquired Immunodeficiency Syndrome and Burkitt's Lymphoma Constitutively Secrete Large Quantities of Interleukin–10," Blood 80(5): 1289–1298 (1992).
Bowie, J.U. et al., "Deciphering the Message in Protein Sequences: Tolerance to Amino Acid Substitutions," Science 247:1306–1310 (1990).

Clark–Lewis, I. et al., "Structural Requirements for Interleukin–8 Function Identified by Design of Analogs and CXC Chemokine Hybrids," J. Biol. Chem. 269:16075–16081 (1994).
Cunningham, B.C. and Wells, J.A., "High–resolution epitope mapping of hGH–receptor interactions by alanine–scanning mutagenesis," Science 244:1081–1085 (1989).
de Waal Malefyt, R. et al., "Interleukin 10 (IL–10) and Viral IL–10 Strongly Reduce Antigen–specific Human T Cell Proliferation by Diminishing the Antigen–presenting Capacity of Monocytes via Downregulation of Class II Major Histocompatibility Complex Expression," J. Exp. Med. 174(4):915–924 (1991).
de Waal Malefyt, R. et al., "Interleukin 10 (IL–10) Inhibits Cytokine Synthesis by Human Monocytes: An Autoregulatory Role of IL–10 Produced by Monocytes," J. Exp. Med. 174(5):1209–1220 (1991).
Feng, L. et al., "Molecular Cloning of Rat Cytokine Synthesis Inhibitory Factor (IL–10) cDNA and Expression in Spleen and Macrophages," Biochem. Biophys. Res. Commun. 192(2):452–458 (1993).
Fiorentino, D.F. et al., "Two Types of Mouse T Helper Cell, IV. Th2 Clones Secrete a Factor that Inhibits Cytokine Production by Th1 Clones," J. Exp. Med. 170:2081–2095 (1989).
Fiorentino, D.F. et al., "IL–10 Inhibits Cytokine Production by Activated Macrophages," J. Immunol. 147(11):3815–3822 (1991).
Gayle III, R.B. et al., "Identification of Regions in Interleukin–1α Important for Activity," J. Biol. Chem. 268(29):22105–22111 (1993).
George, D.G. et al., "Current Methods in Sequence Comparison and Analysis," in Macromolecular Sequencing and Synthesis, Selected Methods and Applications, Schlesinger, D.H., ed., Alan R. Liss, Inc., New York, NY, Chapter 12, pp. 127–149 (1988).
Gronenborn, A.M. et al., "Site directed mutants of human interleukin–1α: a $^1$H–NMR and receptor binding study," FEBS Lett. 231(1):135–138 (1988).
Harlow, E. and Lane, D., Antibodies: A Laboratory Manual, Cold Spring Harbor Laboratory, Cold Spring Harbor, NY, p. 76 (1988).
Hash, S.M. et al., "Characterization of a cDNA encoding bovine interleukin 10: kinetics of expression in bovine lymphocytes," Gene 139:257–261 (1994).
Hayakawa, K. and Hardy, R.R., "Normal, Autoimmune, and Malignant CD5$^+$ B Cells: The Ly–1 B Lineage?" Ann. Rev. Immunol. 6:197–218 (1988).

(List continued on next page.)

Primary Examiner—Prema Mertz
(74) Attorney, Agent, or Firm—Sterne, Kessler, Goldstein & Fox P.L.L.C.

(57) ABSTRACT

The present invention concerns a novel human cytokine. In particular, isolated nucleic acid molecules are provided encoding interleukin-19 (IL-19). IL-19 polypeptides are also provided, as are vectors, host cells and recombinant methods for producing the same. The invention further concerns therapeutic methods for modulating cytokine production.

64 Claims, 6 Drawing Sheets

OTHER PUBLICATIONS

Heinz, D.W. et al., "Folding and function of a T4 lysozyme containing 10 consecutive alanines illustrate the redundancy of information in an amino acid sequence," *Proc. Natl. Acad. Sci. USA* 89:3751–3755 (1992).

Hellyer, N.J. et al., "Cloning of the rat ErbB3 cDNA and characterization of the recombinant protein," *Gene* 165:279–284 (1995).

Hisatsune, T. et al., "A Suppressive Lymphokine Derived from $T_s$ Clone 13G2 Is IL–10," *Lymphokine Cytokine Res.* 11(2):87–93 (1992).

Ishida, H. et al., "Continuous Anti–Interleukin 10 Antibody Administration Depletes Mice of Ly–1 B Cells but Not Conventional B Cells," *J. Exp. Med.* 175(5):1213–1220 (1992).

Kruse, N. et al., "Two distinct functional sites of human interleukin 4 are identified by variants impaired in either receptor binding or receptor activation," *EMBO J.* 12(13):5121–5129 (1993).

Larsen, G.R. et al., "Variants of Human Tissue–type Plasminogen Activator," *J. Biol. Chem.* 263(2):1023–1029 (1988).

Lin, T.–Z. et al., "Cytokines in NZB $CD5^+$ B Clones," *Ann. N.Y. Acad. Sci.* 651:581–583 (1992).

MacNeil, I.A. et al., "IL–10, a Novel Growth Cofactor for Mature and Immature T Cells," *J. Immunol.* 145(12):4167–4173 (1990).

Moore, K.W. et al., "Homology of Cytokine Synthesis Inhibitory Factor (IL–10) to the Epstein–Barr Virus Gene BCRFI," *Science* 248:1230–1234 (1990).

Moore, K.W. et al., *Science* 250:494 (1990). Erratum to Moore, K.W. et al., "Homology of Cytokine Synthesis Inhibitory Factor (IL–10) to the Epstein–Barr Virus Gene BCRFI," *Science* 248:1230–1234 (1990).

Mosley, B. et al., "Determination of the minimum polypeptide lengths of the functionally active sites of human interleukins 1α and 1β," *Proc. Natl. Acad. Sci. USA* 84:4572–4576 (1987).

O'Garra, A. et al., "Production of cytokines by mouse B cells: B lymphomas and normal B cells produce interleukin 10," *Int. Immunol.* 2(9):821–832 (1990).

Ralph, P. et al., "IL–10, T Lymphocyte Inhibitor of Human Blood Cell Production of IL–1 and Tumor Necrosis Factor," *J. Immunol.* 148(3):808–814 (1992).

Salgame, P. et al., "Differing Lymphokine Profiles of Functional Subsets of Human CD4 and CD8 T Cell Clones," *Science* 254:279–282 (1991).

Suda, T. et al., "Identification of a Novel Thymocyte Growth–Promoting Factor Derived from B Cell Lymphomas," *Cell. Immunol.* 129:228–240 (1990).

Tartaglia, L.A. et al., "Identification and Expression Cloning of a Leptin Receptor, OB–R," *Cell* 83:1263–1271 (Dec. 1995).

Vieira, P. et al., "Isolation and expression of human cytokine synthesis inhibitory factor cDNA clones: Homology to Epstein–Barr virus open reading frame BCRFI," *Proc. Natl. Acad. Sci. USA* 88:1172–1176 (1991).

Wang, S.C. et al., "FK 506, Rapamycin, and Cyclosporine: Effects on IL–4 and IL–10 mRNA Levels in a T–Helper 2 Cell Line," *Transplantation Proc.* 23(6):2920–2922 (1991).

Yamamura, M. et al., "Defining Protective Responses to Pathogens: Cytokine Profiles in Leprosy Lesions," *Science* 254:277–279 (1991).

Yssel, H. et al., "IL–10 is Produced by Subsets of Human $CD4^+$ T Cell Clones and Peripheral Blood T Cells," *J. Immunol.* 149(7):2378–2384 (1992).

Zurawski, S.M. et al., "Alterations in the Amino–Terminal Third of Mouse Interleukin 2: Effects on Biological Activity and Immunoreactivity," *J. Immunol.* 137(10):3354–3360 (1986).

Zurawski, S.M. and Zurawski, G., "Mouse interleukin–2 structure–function studies: substitutions in the first α–helix can specifically inactivate p70 receptor binding and mutations in the fifth α–helix can specifically inactivate p55 receptor binding," *EMBO J.* 8(9)2583–2590 (1989).

Zurawski, S.M. et al., "Definition and spatial location of mouse interleukin–2 residues that interact with its heterotrimeric receptor," *EMBO J.* 12(13):5113–5119 (1993).

International Search Report for Application No. PCT/US96/14355, mailed Dec. 1996.

NCBI Entrez, GenBank Report, Accession No. AA151733, from Hillier, L. et al. (Dec. 1996).

NCBI Entrez, GenBank Report, Accession No. AA151652, from Hillier, L. et al. (Dec. 1996).

NCBI Entrez, GenBank Report, Accession No. AA151656, from Hillier, L. et al. (May 1997).

NCBI Entrez, GenBank Report, Accession No. AA151736, from Hillier, L. et al. (May 1997).

\* cited by examiner

```
GGCACGAGCACAAGGAGCAGCCCGCAAGCACCAAGTGAGAGGCATGAAGTTACAGTGTGT 60
                                              M  K  L  Q  C  V

TTCCCTTTGGCTCCTGGGTACAATACTGATATTGTGCTCAGTAGACAACCACGGTCTCAG 120
 S  L  W  L  L  G  T  I  L  I  L  C  S  V  D  N  H  G  L  R

GAGATGTCTGATTTCCACAGACATGCACCATATAGAAGAGAGTTTCCAAGAAATCAAAAG 180
 R  C  L  I  S  T  D  M  H  H  I  E  E  S  F  Q  E  I  K  R

AGCCATCCAAGCTAAGGACACCTTCCCAAATGTCACTATCCTGTCCACATTGGAGACTCT 240
 A  I  Q  A  K  D  T  F  P  N  V  T  I  L  S  T  L  E  T  L

GCAGATCATTAAGCCCTTAGATGTGTGCTGCGTGACCAAGAACCTCCTGGCGTTCTACGT 300
 Q  I  I  K  P  L  D  V  C  C  V  T  K  N  L  L  A  F  Y  V

GGACAGGGTGTTCAAGGATCATCAGGAGCCAAACCCCAAAATCTTGAGAAAAATCAGCAG 360
 D  R  V  F  K  D  H  Q  E  P  N  P  K  I  L  R  K  I  S  S

CATTGCCAACTCTTTCCTCTACATGCAGAAAACTCTGCGGCAATGTCAGGAACAGAGGCA 420
 I  A  N  S  F  L  Y  M  Q  K  T  L  R  Q  C  Q  E  Q  R  Q

GTGTCACTGCAGGCAGGAAGCCACCAATGCCACCAGAGTCATCCATGACAACTATGATCA 480
 C  H  C  R  Q  E  A  T  N  A  T  R  V  I  H  D  N  Y  D  Q

GCTGGAGGTCCACGCTGCTGCCATTAAATCCCTGGGAGAGCTCGACGTCTTTCTAGCCTG 540
 L  E  V  H  A  A  A  I  K  S  L  G  E  L  D  V  F  L  A  W

GATTAATAAGAATCATGAAGTAATGTCCTCAGCTTGATGACAAGGAACCTGTATAGTGAT 600
 I  N  K  N  H  E  V  M  S  S  A

CCAGGGATGAACACCCCCTGTGCGGTTTACTGTGGGAGACAGCCCACCTTGAAGGGGAAG 660

GAGATGGGGAAGGCCCCTTGCAGCTGAAAGTCCCACTGGCTGGCCTCAGGCTGTCTTATT 720

CCGCTTGAAAATAGCCAAAAAGTCTACTGTGGTATTTGTAATAAACTCTATCTGCTGAAA 780

GGGCCTGCAGGCCATCCTGGGAGTAAAGGGCTGCCTTCCCATCTAATTTATTGTGAAGTC 840

ATATAGTCCATGTCTGTGATGTGAGCCAAGTGATATCCTGTAGTACACATTGTACTGAGT 900

GGTTTTTCTGAATAAATTCCATATTTTACCTATGGAAAAAAAAAAAAAAAAAAAAAAAA 960

AAAAAA 966
```

FIG. 1

|           | 1          | 11         | 21         | 31         | 41         |
|-----------|------------|------------|------------|------------|------------|
| hIL-10    | MHSSALLC.C | LVLLTGVRA  | SPGQGTQSEN | SCTHFPGNLP | NMLRDLRDAF |
| HMQBM23   | MK...LQCVS | LWLLGTILI  | LCSVDNHGLR | RCL.....IS | TDMHHIEESF |
| Consensus | M----L-C - | L-LL------ | ---------- | -C-------- | --------F  |

|           | 51         | 61         | 71         | 81         | 91         |
|-----------|------------|------------|------------|------------|------------|
| hIL-10    | SRVKTFFQMK | DQLDNLLLKE | SL..LEDFKG | YLGCQALSEM | IQFYLEEVMP |
| HMQBM23   | QEIKRAIQAK | DTFPNVTILS | TLETLQIIKP | LDVCCVTKNL | LAFYVDRVFK |
| Consensus | ---K---Q-K | D---N----- | -L--L---K- | ---C------ | --FY---V-- |

|           | 101        | 111        | 121        | 131        | 141        |
|-----------|------------|------------|------------|------------|------------|
| hIL-10    | QAENQDPDIK | AHVNSLGENL | KTLRLRLRRC | HRFLPC...E | NKSKAVEQVK |
| HMQBM23   | DHQEPNPKIL | RKISSIANSF | LYMQKTLRQC | QEQRQCHCRQ | EATNATRVIH |
| Consensus | ------P-I- | ----S----- | ------LR-C | -----C---- | ----A----- |

|           | 151        | 161        | 171        | 181        |
|-----------|------------|------------|------------|------------|
| hIL-10    | NAFNKLQ.EK | GIYKAMSEFD | IFINYIE.AY | MTMKIRN    |
| HMQBM23   | DNYDQLEVHA | AAIKSLGELD | VFLAWINKNH | EVMSSA     |
| Consensus | -----L---- | ---K---E-D | -F---I---- | --M----    |

FIG.5

INTERLEUKIN-19

This application is a division of U.S. application Ser. No. 08/921,382, filed Aug. 29, 1997, now U.S. Pat. No. 5,985,614, which disclosure is herein incorporated by reference; said application Ser. No. 08/921,382 claims the benefit of U.S. Provisional Appl. No. 60/024,882, filed Aug. 30, 1996, which disclosure is herein incorporated by reference.

BACKGROUND OF THE INVENTION

1. Field of the Invention

The present invention concerns a novel human cytokine. In particular, isolated nucleic acid molecules are provided encoding interleukin-19 (IL-19). IL-19 polypeptides are also provided, as are vectors, host cells and recombinant methods for producing the same. The invention further concerns therapeutic methods for modulating cytokine production.

2. Related Art

Interleukin-10 (IL-10) is a pleiotropic cytokine that has been implicated as an important regulator of the functions of lymphoid and myeloid cells. IL-10 blocks activation of cytokine synthesis and several accessory functions of macrophages, thus acting as a potent suppressor of the effector functions of macrophages, T cells and NK cells. IL-10 has also been implicated in the regulation of differentiation of B cells, mast cells and thymocytes.

IL-10 was identified independently in two different lines of experiments. One of these identified a B-cell-derived mediator which co-stimulated active thymocytes (Suda et al., *Cell Immunol.* 129:228 (1990)). The other identification determined that IL-10 is involved in the cross-regulation between two often mutually exclusive effector arms of immunity carried out by T helper (CD4$^+$) subpopulations, Th1 (involved in cell-mediated immune responses) and Th2 (involved in antibody-mediated immune responses). In this role, IL-10 is expressed by Th2 cells and functions to suppress cytokine production by Th1 cells, an activity termed cytokine synthesis inhibitory factor (CSIF) activity.

cDNA clones encoding murine IL-10 (mIL-10) were isolated based on the expression of CSIF activity (Moore et al., *Science* 248:1230–34 (1990)). cDNA clones encoding human IL-10 (hIL-10) were subsequently identified by cross-hybridization with the mouse cDNA (Vieira et al., *Proc. Natl. Acad. Sci USA* 88:1172–1176 (1991)). mIL-10 is expressed by mouse CD4$^+$ Th2 cells, at least one CD8$^+$ clone, B lymphomas, T cells, activated mast cell lines, activated macrophages, keratinocytes, and Ly-1 B (B-1) cells (Fiorentino, D. F. et al., *J. Exp. Med.* 170:2081 (1989); (Moore et al., *Science* 248:1230–34 (1990); 87–93 (1992); Lin et al., *Ann. N.Y. Acad. Sci.* 651 O'Garra et al. *Int. Immunol.* 2: 821–832 (1990); MacNeil et al., *J. Immunol.* 145: 4167–4173 (1990); Fiorentino et al., *J. Immunol.* 147:3815–3822 (1991); Hisatsune et al, *Lymphokine Cytokine Res.* 11:651–683 (1992)). hIL-10 is expressed by human CD4$^+$ T cells and Th0, Th1, and Th2 T cell clones, by CD8$^+$ T cells and clones (Yssel et al., *J. Immunol.*), monocytes/macrophages, keratinocytes, activated B cells, B lymphomas, and Burkitt lymphoma lines infected with a transforming EBV strain, but not with a non-transforming strain (Vieira, P. et al., *Proc. Natl. Acad. Sci. USA* 88:1172–76 (1991); de Waal-Malefyt, R. et al., *J. Exp. Med.* 174:1209–20 (1991); de Waal-Malefyt, R. et al., *J. Exp. Med.* 174:915–24 (1991); Salgame, P. et al, *Science* 254:279–82 (1991); Yamamura, M. et al., *Science* 254:277–79 (1991); Ralph, P. et al.,*J. Immunol.* 148:808–14 (1992); Benjamin, D. et al., *Blood* 80:1289–98 (1992)).

Thus, IL-10 is not strictly a Th2-specific cytokine, and its pattern of expression resembles IL-6 more than IL-4 or IL-5 (Wang, S. C. et al., *Transplant. Proc.* 23:2920–22 (1991)). Like IL-6 but unlike most other T cell derived cytokines, IL-10 expression is not inhibited by cyclosporin or FK-506 (Wang, S. C. et al., *Transplant Proc.* 23:2920 (1991)).

In an attempt to determine the in vivo role of IL-10, normal mice were treated from birth to adulthood with IL-10-neutralizing antibodies (Wang, S. C. et al., *Transplant Proc.* 23:2920 (1991); Ishida, H. et al., *J. Exp. Med.* 175:1213 (1992)) The resulting phenotypic changes included an increased level of circulating IFN-γ, TNF-α and IL-6, reduced serum IgM and IgA, a marked depletion of peritoneal B cells, and an inability to develop in vivo antibody responses to two bacterial antigens known be combatted with antibody produced by peritoneal B cells (Hayakawa, K. et al., *Annu. Rev. Immunol.* 6:197 (1988)). The reduction in peritoneal B cells was determined to be a consequence of IFN-γ elevation (Ishida, H. et al., *J. Exp. Med.* 175:1213 (1992)).

Other experiments have shown that IL-10 suppresses in vitro production of inflammatory monokines such as TNF-α and IL-1. This data corresponds to in vivo studies which show that IL-10 antagonists elevate the same inflammatory monokines. These results predict a strong anti-inflammatory role for IL-10. In addition, IL-10 antagonists may be useful to enhance Th1 immunity, which could be beneficial in infectious diseases of viral origin, or diseases involving intracellular pathogens.

The diverse biological activities of IL-10 have led to predictions that both IL-10 and its antagonists will have a wide range of clinical applications. It is clear that there is a continuing need in the art for isolating novel cytokines capable of mediating such diverse biological processes.

SUMMARY OF THE INVENTION

The present invention provides isolated nucleic acid molecules comprising a polynucleotide encoding a human IL-19 polypeptide having the amino acid sequence in FIG. 1 [SEQ ID NO: 2] or the amino acid sequence encoded by the cDNA clone deposited as ATCC Deposit Number 97662 on Jul. 17, 1996. The nucleotide sequence determined by sequencing the deposited IL-19 cDNA clone, which is shown in FIG. 1 [SEQ ID NO: 1], contains an open reading frame encoding a polypeptide of about 177 amino acid residues including an initiation codon at nucleotide positions 44–46, a leader sequence of about 24 amino acid residues and a deduced molecular weight of about 20.4 kDa. The 153 amino acid sequence of the predicted mature IL-19 protein is shown in FIG. 1 (last 153 residues) and in SEQ ID NO:2 (from amino acid residue 1 to residue 153).

The present invention also relates to recombinant vectors which include the isolated nucleic acid molecules of the present invention and to host cells containing the recombinant vectors, as well as to methods of making such vectors and host cells and for using them for production of IL-19 polypeptides or peptides by recombinant techniques.

The invention further provides an isolated IL-19 polypeptide having an amino acid sequence encoded by a polynucleotide described herein.

IL-19, which is secreted, and which has significant homology to IL-10, is believed by the present inventors to be expressed only, or at least primarily, in activated monocytes (FIG. 4). Thus, detecting IL-19 gene expression in cells of the immune system is useful for identifing activated monocytes. Further, for a number of disorders, it is believed by the inventors that significantly higher or lower levels of IL-19 gene expression can be detected in bodily fluids (e.g., serum, plasma, urine, synovial fluid or spinal fluid) taken from an individual having such a disorder, relative to a "standard" IL-19 gene expression level, i.e., the IL-19 expression level in bodily fluids from an individual not having the disorder. Thus, the invention provides a diagnostic method useful during diagnosis of a disorder related to an abnormal level of IL-19 gene expression, which involves (a) assaying IL-19 gene expression level in cells or body fluid of that individual; (b) comparing that IL-19 gene expression level with a standard IL-19 gene expression level, whereby an increase or decrease in the assayed IL-19 gene expression level compared to the standard expression level is indicative of a disorder. An additional aspect of the invention is related to a method for treating an individual in need of an increased level of IL-19 activity in the body, which involves administering to such an individual a composition comprising an IL-19 polypeptide of the invention. A still further aspect of the invention is related to a method of treating an individual in need of a decreased level of IL-19 activity in the body, which involves administering to such an individual a composition comprising an antagonist to IL-19 such as anti-IL-19 antibodies.

BRIEF DESCRIPTION OF THE FIGURES

FIG. 1 shows the nucleotide [SEQ ID NO: 1] and deduced amino acid [SEQ ID NO:2] sequences of the complete IL-19 protein determined by sequencing of the DNA clone contained in ATCC Deposit No. 97662. The protein has a leader sequence of about 24 amino acid residues (underlined) and a deduced molecular weight of about 20.4 kDa. The amino acid sequence of the predicted mature IL-19 protein is also shown in FIG. 1 (last 153 amino acids) [SEQ ID NO:2].

FIG. 5 shows the regions of similarity between the amino acid sequences of the IL-19 protein and human IL-10 (hIL-10) [SEQ ID NO: 3].

DETAILED DESCRIPTION OF THE INVENTION

Figure 2:
FIG. 2 is a protein gel showing IL-19 protein expressed from E. coli strain M15rep4 (see Example 1).

The present invention provides isolated nucleic acid molecules comprising a polynucleotide encoding the IL-19 protein having the amino acid sequence shown in FIG. 1 [SEQ ID NO:2] which was determined by sequencing a cloned cDNA. The IL-19 protein of the present invention shares sequence homology with human IL-10 (FIG. 5) [SEQ ID NO:3]. The nucleotide sequence shown in FIG. 1 [SEQ ID NO:1] was obtained by sequencing the HMQBM23 cDNA clone encoding an IL-19 polypeptide, which was deposited on Jul. 17, 1996 at the American Type Culture Collection, Patent Depository, 10801 University Boulevard, Manassas, Va. 20110-2209 and given accession number 97662. The deposited clone is contained in the pBluescript SK(−) plasmid (Stratagene, La Jolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain a some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIG. 1, a nucleic acid molecule of the present invention encoding an IL-19 polypeptide may be obtained using standard cloning and screening procedures, such as those for cloning cDNAs using mRNA as starting material. Illustrative of the invention, the nucleic acid molecule described in FIG. 1 [SEQ ID NO: 1] was discovered in a cDNA library derived from human activated monocytes. The determined nucleotide sequence of the IL-19 cDNA of FIG. 1 contains an open reading frame encoding a protein of about 177 amino acid residues with an initiation codon at positions 44–46 of the nucleotide sequence shown in FIG. 1 [SEQ ID NO. 1], and a predicted leader sequence of about 24 amino acid residues, and a deduced molecular weight of about 20.4 kDa. The amino acid sequence of the predicted mature IL-19 protein is from about amino acid residue 25 to about residue 177 shown in FIG. 1 or amino acids 1–153 shown in SEQ ID NO:2. The IL-19 protein shown in FIG. 1 [SEQ ID NO:2] is about 20% identical and about 46% similar to human IL-10 (FIG. 5).

The present invention also provides the mature form(s) of the IL-19 protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature IL-19 polypeptides having the amino acid sequence encoded by the cDNA clone contained in the host identified as ATCC Deposit No. 97662 and as shown in SEQ ID NO:2. By the mature IL-19 protein having the amino acid sequence encoded by the CDNA clone contained in the host identified as ATCC Deposit 97662 is meant the mature form(s) of the IL-19 protein produced by expression in a mammalian cell (e.g., COS cells, as described below) of the complete open reading frame encoded by the human DNA sequence of the clone contained in the vector in the deposited host. As indicated below, the mature IL-19 having the amino acid sequence encoded by the CDNA clone contained in ATCC Deposit No. 97662 may or may not differ from the predicted "mature" IL-19 protein shown in SEQ ID NO:2 (amino acids from about 1 to about 153) depending on the accuracy of the predicted cleavage site based on computer analysis.

Methods for predicting whether a protein has a secretory leader as well as the cleavage point for that leader sequence are available. For instance, the methods of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the complete IL-19 polypeptides of the present invention were analyzed by a computer program ("PSORT") (K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage site between amino acids −1 and 1 in SEQ ID NO:2. Thereafter, the complete amino acid sequences were further analyzed by visual inspection, applying a simple form of the (−1,−3) rule of von Heinje. von Heinje, supra. Thus, the leader sequence for the IL-19 protein is predicted to consist of amino acid residues from about −24 to about −1 in SEQ ID NO:2, while the mature IL-19 protein is predicted to consist of residues from about 1 to about 153.

As one of ordinary skill would appreciate, due to the possibilities of sequencing errors discussed above, as well as the variability of cleavage sites for leaders in different known proteins, the actual IL-19 polypeptide encoded by the deposited cDNA comprises about 177 amino acids, but may be anywhere in the range of 170–183 amino acids; and the actual leader sequence of this protein is about 24 amino acids, but may be anywhere in the range of about 18 to about 29 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 44–46 of the nucleotide sequence shown in FIG. 1 [SEQ ID NO:1]; DNA molecules comprising the coding sequence for the mature IL-19 protein shown in FIG. 1 (last 153 amino acids) [SEQ ID NO:2]; and DNA molecules which comprise a sequence substantially different from those described above but which, due to the degeneracy of the genetic code, still encode the IL-19 protein. Of course, the genetic code is well known in the art. Thus, it would be routine for one skilled in the art to generate the degenerate variants described above.

In addition, the invention provides nucleic acid molecules having nucleotide sequences related to extensive portions of SEQ ID NO:1 which have been determined from the following related cDNA clones: PO14 (SEQ ID NO:16).

Sequences of public ESTs that relate to a portion of SEQ ID NO:1 have the following GenBank Accession Numbers: AA151656 (SEQ ID NO:12), AA151652(SEQ ID NO:13), AA151733 (SEQ ID NO:14), and AA151736 (SEQ ID NO:15).

In another aspect, the invention provides isolated nucleic acid molecules encoding the IL-19 polypeptide having an amino acid sequence encoded by the cDNA clone contained in the plasmid deposited as ATCC Deposit No. 97662 on Jul. 17, 1996. In a further embodiment, nucleic acid molecules are provided encoding the mature IL-19 polypeptide or the full-length IL-19 polypeptide lacking the N-terminal methionine. The invention also provides an isolated nucleic acid molecule having the nucleotide sequence shown in SEQ ID NO:1 or the nucleotide sequence of the above-described deposited cDNA clone. The invention further provides an isolated nucleic acid molecule having the nucleotide sequence shown in FIG. 1 [SEQ ID NO: 1] or the nucleotide sequence of the IL-19 cDNA contained in the above-described deposited clone, or nucleic acid molecule having a sequence complementary to one of the above sequences. Such isolated molecules, particularly DNA molecules, are useful as probes for gene mapping by in situ hybridization with chromosomes and for detecting expression of the IL-19 gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in SEQ ID NO:1 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925 or 950 nt in length are also useful according to the present invention as are fragments corresponding to most, if not all, of the nucleotide sequence of the deposited cDNA or as shown in SEQ ID NO:1. By a fragment at least 20 nt in length, for example, is intended fragments which include 20 or more contiguous bases from the nucleotide sequence of the deposited cDNA or the nucleotide sequence as shown in SEQ ID NO:1.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 97662. By "stringent hybridization conditions" is intended overnight incubation at 42° C. in a solution comprising: 50% formamide, 5× SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1× SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO:1). Of course, a polynucleotide which hybridizes only to a poly A sequence (such as the 3' terminal poly(A) tract of the IL-19 cDNA shown in SEQ ID NO:1), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

Since an IL-19 cDNA clone has been deposited and its determined nucleotide sequence is provided in FIG. 1 [SEQ ID NO:1], generating polynucleotides which hybridize to a portion of the IL-19 cDNA molecule would be routine to the skilled artisan. For example, restriction endonuclease cleavage or shearing by sonication of the IL-19 cDNA clone could easily be used to generate DNA portions of various sizes which are polynucleotides that hybridize to a portion of the IL-19 cDNA molecule. Alternatively, the hybridizing polynucleotides of the present invention could be generated synthetically according to known techniques. Of course, a polynucleotide which hybridizes only to a poly A sequence (such as the 3' terminal poly(A) tract of the IL-19 cDNA shown in FIG. 1 [SEQ ID NO: 1]), or to a complementary stretch of T (or U) resides, would not be included in a polynucleotide of the invention used to hybridize to a portion of a nucleic acid of the invention, since such a polynucleotide would hybridize to any nucleic acid molecule contain a poly (A) stretch or the complement thereof (e.g., practically any double-stranded cDNA clone).

Preferred nucleic acid fragments of the present invention include nucleic acid molecules encoding epitope-bearing portions of the IL-19 protein. In particular, such nucleic acid fragments of the present invention include nucleic acid molecules encoding: a polypeptide comprising amino acid residues from about −5 to about 4 in SEQ ID NO:2; a polypeptide comprising amino acid residues from about 64 to about 82 in SEQ ID NO:2; and a polypeptide comprising amino acid residues from about 115 to about 125 in SEQ ID NO:2. The inventors have determined that the above polypeptide fragments are antigenic regions of the IL-19 protein. Methods for determining other such epitope-bearing portions of the IL-19 protein are described in detail below.

As indicated, nucleic acid molecules of the present invention which encode the IL-19 polypeptide may include, but are not limited to those encoding the amino acid sequence of the mature polypeptide, by itself; the coding sequence for the mature polypeptide and additional sequences, such as those encoding the about 24 amino acid leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al. *Proc. Natl. Acad. Sci., USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767–768 (1984). As discussed below, other such fusion proteins include the IL-19 fused to Fc at the N- or C-terminus.

The present invention further relates to variants of the nucleic acid molecules of the present invention, which encode portions, analogs or derivatives of the IL-19 protein. Variants may occur naturally, such as a natural allelic variant. By an "allelic variant" is intended one of several alternate forms of a gene occupying a given locus on a chromosome of an organism. *Genes II*, Lewin, ed. Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions. Especially preferred among these are silent substitutions, additions and deletions, which do not alter the properties and activities of the IL-19 protein or portions thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical to a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence at positions from about 1 to about 153 in SEQ ID NO:2; (d) a nucleotide sequence encoding the polypeptide having the amino acid sequence encoded by the cDNA clone contained in ATCC Deposit No. 97662; (e) a nucleotide sequence encoding the mature IL-19 polypeptide having the amino acid sequence encoded by the cDNA clone contained in ATCC Deposit No. 97662; or (f) a nucleotide sequence complementary to any of the nucleotide sequences in (a), (b), (c), (d) or (e).

By a polynucleotide having a nucleotide sequence at least, for example, 95% "identical" to a reference nucleotide sequence encoding an IL-19 polypeptide is intended that the nucleotide sequence of the polynucleotide is identical to the reference sequence except that the polynucleotide sequence may include up to five point mutations per each 100 nucleotides of the reference nucleotide sequence encoding the IL-19 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman (Advances in Applied Mathematics 2: 482489, 1981) to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 1 [SEQ ID NO: 1] or to the nucleic acid sequence of the deposited cDNA, irrespective of whether they encode a polypeptide having IL-19 activity. This is because, even where a particular nucleic acid molecule does not encode a polypeptide having IL-19 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having IL-19 activity include, inter alia, (1) isolating the IL-19 gene or allelic variants thereof in a cDNA library; (2) in situ hybridization (e.g., "FISH") to metaphase chromosomal spreads to provide precise chromosomal location of the IL-19 gene as described in Verma et al., Human Chromosomes: a Manual of Basic Techniques, Pergamon Press, New York (1988); and (3) Northern Blot analysis for detecting IL-19 mRNA expression in specific cell types (e.g., activated monocytes).

Preferred, however, are nucleic acid molecules having sequences at least 90%, 95%, 96%, 97%, 98% or 99% identical to the nucleic acid sequence shown in FIG. 1 [SEQ ID NO:1] or to the nucleic acid sequence of the deposited cDNA which do, in fact, encode a polypeptide having IL-19 protein activity. By "a polypeptide having IL-19 activity" is intended polypeptides exhibiting activity similar, but not necessarily identical, to an activity of the IL-19 protein of the invention (either the full-length protein or, preferably, the mature protein) as measured in a particular biological assay.

IL-19 exhibits several biological activities which could form the basis of such biological assays. In particular, it is believed by the inventors that IL-19 has the property of modulating the synthesis of at least one cytokine in the group consisting of IFN-γ, lymphotoxin, IL-2, IL-3, and GM-CSF in a population of T helper cells induced to synthesize one or more of these cytokines by exposure to syngeneic antigen-presenting cells (APCs) and antigen. In this activity, APCs are treated so that they become incapable of replication, but their antigen-processing machinery remains functional. This is conveniently accomplished by irradiating the APCs, e.g. with about 1500–3000 R (gamma or X-radiation) before mixing with the T-cells.

Alternatively, changes in levels of cytokine production may be assayed in primary or, preferably, secondary mixed-lymphocyte reactions (MLR), in which case syngeneic APCs need not be used. MLRs are well-known in the art, e.g., Bradley, pp 162–166 in Mishell et al., eds. Selected Methods in Cellular Immunology (Freeman, San Francisco, 1980); and Battisto, et al., Meth, in Enzymol. 150:83–91 (1987). Briefly, the cell populations are mixed, one of the populations having been treated prior to mixing to prevent proliferation, e.g., by irradiation. Preferably, the cell populations are prepared at a concentration of about $2 \times 10^6$ cells/ml in supplemented media, e.g. RPMI 1640 with 10% fetal calf serum. For both controls and test cultures, mix 0.05 ml of each population for the assay. For a secondary MLR, the cells remaining after 7 days in the primary MLR are re-stimulated by freshly prepared, irradiated stimulator cells. The sample suspected of containing IL-19 may be added to the test cultures at the time of mixing, and both controls and test cultures may be assayed for cytokine production from 1–3 days after mixing.

Obtaining T cell populations and/or APC populations for IL-19 assays employs techniques well known in the art which are fully described in DiSabato et a;., eds., Meth. in Enzymol. Vol. 108 (1984). APCs for the preferred IL-19 assay are peripheral blood monocytes. These are obtained using standard techniques, e.g. as described by the following articles in the aforementioned DiSabato et a;., eds., Meth. in Enzymol. Vol. 108 (1984): Boyum, pp. 88–102; Mage, pp. 118–132; Litvin et al., pp. 298–302; Stevenson, pp. 242–249; and Romain, pp. 148–153, which references are herein incorporated by reference. Preferably, helper T-cells are used in the IL-19 assays, which are obtained by first separating lymphocytes from the peripheral blood, and then selecting, e.g., by panning or flow cytometry, helper cells using a commercially available anti-CD4 antibody, e.g. OKT4, described in U.S. Pat. No. 4,381,295, and available form Ortho Pharmaceutical Corp. The requisite techniques are fully disclosed by Boyum in *Scand. JL. Clin. Lab. Invest.,* 21(Suppl. 97):77 (1968) and in *Meth. in Enzymol. Vol.* 108 (1984) (cited above) and by Bram et al., *Meth. in Enzymol.* 121:737–748 (1986). Generally, PBLs are obtained from fresh blood by Ficoll-Hypaque density gradient centrifugation.

A variety of antigens can be employed in the assay, e.g. Keyhole limpet hemocyanin (KLH), fowl γ-globulin, or the like. More preferably, in place of antigen, helper T cells are stimulated with anti-CD3 monoclonal antibody, e.g. OKT3 disclosed in U.S. Pat. No. 4,361,549, in the assay.

Cytokine concentrations in control and test samples are measured by standard biological and/or immunochemical assays. Construction of immunochemical assays for specific cytokines is well known in the art when the purified cytokine is available; e.g. Campbell, Monoclonal Antibody Technology (Elsevier, Amsterdam, 1984); Tijssen, Practice and Theory of Enzyme Immunoassays (Elsevier, Amsterdam, 1985); and U.S. Pat. No. 4,486,530, are examples of the extensive literature on the subject. ELISA kits for human IL-2, human IL-3, and human GM-CSF are commercially available from Genzyme Corp. (Boston, Mass.); and an ELISA kit for human IFN-γ is commercially available from Endogen, Inc. (Boston, Mass.). Polyclonal antibodies specific for human lymphotoxin are available from genzyme, Corp., which can be used in a radioimmunoassay for human lymphotoxin, e.g., Chard, An Introduction to Radioimmunoassay and Related Techniques (Elsevier, Amsterdam, 1982).

Biological assays of the cytokines listed above can also be used to determine whether a sample has IL-19 activity, i.e, whether a sample modulates cytokine expression or activity in a manner similar to IL-19. A biological assay for human lymphotoxins disclosed by Aggarwal, *Meth. in Enzymol.* 116:441–447 (1985), and by Matthews et al., in *Lymphokines and Interferons: A Practical Approach,* Clemens et al., eds, IRL Press, Washington, D.C., 1987, pp. 221–225. Human IL-2 and GM-CSF can be assayed with factor-dependent cell lines CTLL-2 and KG-1, available from the ATCC under accession numbers TIB 214 and CCL246, respectively. Human IL-3 can be assayed by its ability to simulate the formation of a wide range of hematopoietic cell colonies in soft agar cultures, e.g. as described by MEtcalf, The Hematopoietic Colony Stimulating Factors (Elsevier, Amsterdam, 1984). IFN-γ can be quantified with anti-viral assays, e.g. Meager, pp. 129–147, in Clemens et al., eds (cited above).

Cytokine production can also be determined by MRNA analysis. Cytokine mRNAs can be measured by cytoplasmic dot hybridization, as described by White et al. (*J. Biol. Chem.* 257:8569–8572 (1982)) and Gillespie et al., U.S. Pat. No. 4,483,920, both of which are hereby incorporated by reference. Other approaches include dot blotting using purified RNA, e.g. Chapter 6 in Hames et al., eds, Nucleic Acid Hybridization: A Practical Approach, IRL PRess, Washington D.C., 1985.

Some samples to be tested for IL-19 activity must be pretreated to remove cytokines that might interfere with the assay. For example, IL-2 increases the production of IFN-γ in some cells. Thus, depending on the T helper cells used in the assay, IL-2 may have to be removed from the sample being tested. Such removals are conveniently accommodated by passing a sample over a standard anti-cytokine affinity column.

Thus, by using an assay such as those described above, the effect of the substance suspected of having IL-19 activity on the activity of any one of a number of cytokines may be compared to the IL-19 protein of the invention, in order to determine if the sample indeed has IL-19 activity.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 [SEQ ID NO: 1] will encode a polypeptide "having IL-19 protein activity." In fact, since degenerate variants of these nucleotide sequences all encode the same polypeptide, this will be clear to the skilled artisan even without performing one of the above-described comparison assays. It will be further recognized in the art that, for such nucleic acid molecules that are not degenerate variants, a reasonable number will also encode a polypeptide having IL-19 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U., et al., "Deciphering the Message in Protein Sequences: Tolerance to Amino Acid Substitutions," *Science* 247:1306–1310 (1990), wherein the authors indicate that were surprisingly tolerant of amino acid substitutions.

Vectors and Host Cells

The present invention also relates to vectors which include the isolated DNA molecules of the present invention, host cells which are genetically engineered with the recombinant vectors, and the production of IL-19 polypeptides or portions thereof by recombinant techniques.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will include a translation initiating AUG at the beginning and a termination codon appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture media and conditions for the above-described host cells are known in the art.

Among vectors preferred for use in bacteria include pA2, pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223–3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the E. coli lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., BASIC METHODS IN MOLECULAR BIOLOGY, (1986).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., Journal of Molecular Recognition 8:52–58 (1995) and K. Johanson et al., The Journal of Biological Chemistry 270(16):9459–9471 (1995).

The IL-19 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

IL-19 Polypeptides and Peptides

The invention further provides an isolated IL-19 polypeptide having the amino acid sequence encoded by the deposited cDNA, or the amino acid sequence in FIG. 1 [SEQ ID NO:2], or a peptide or polypeptide comprising a portion of the above polypeptides. The terms "peptide" and "oligopeptide" are considered synonymous (as is commonly recognized) and each term can be used interchangeably as the context requires to indicate a chain of at least to amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequence of the IL-19 polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the IL-19 polypeptide which show substantial IL-19 polypeptide activity or which include regions of IL-19 protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the IL-19 protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-α to only one of the two known types of TNF receptors. Thus, the IL-19 of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given IL-19 polypeptide will not be more than 50, 40, 30, 25, 20, 15, 10, 5 or 3.

Amino acids in the IL-19 protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the IL-19 polypeptide can be substantially purified by the one-step method described in Smith and Johnson, *Gene* 67:31–40 (1988).

The polypeptides of the present invention include the polypeptide encoded by the deposited cDNA including the leader; the mature polypeptide encoded by the deposited the cDNA minus the leader (i.e., the mature protein); a polypeptide comprising amino acids about −24 to about 153 in SEQ ID NO:2; a polypeptide comprising amino acids about −23 to about 153 in SEQ ID NO:2; a polypeptide comprising amino acids about 1 to about 153 in SEQ ID NO:2; as well as polypeptides which are at least 80% identical, more preferably at least 90% or 95% identical, still more preferably at least 96%, 97%, 98% or 99% identical to those described above and also include portions of such polypeptides with at least 30 amino acids and more preferably at least 50 amino acids.

By a polypeptide having an amino acid sequence at least, for example, 95% "identical" to a reference amino acid sequence of an IL-19 polypeptide is intended that the amino acid sequence of the polypeptide is identical to the reference sequence except that the polypeptide sequence may include up to five amino acid alterations per each 100 amino acids of the reference amino acid of the IL-19 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1 [SEQ ID NO:2] or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention is useful as a molecular weight marker on SDS-PAGE gels or on molecular sieve gel filtration columns using methods well known to those of skill in the art.

As described in detail below, the polypeptides of the present invention can be used to raise polyclonal and monoclonal antibodies, which are useful in diagnostic assays for detecting IL-19 protein expression as described below or as agonists and antagonists capable of enhancing or inhibiting IL-19 protein function. Further, such polypeptides can be used in the yeast two-hybrid system to "capture" IL-19 protein binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, H. M., Meloen, R. H. and Barteling, S. J. (1984) Use of peptide synthesis to probe viral antigens for epitopes to a resolution of a single amino acid. Proc. Natl. Acad. Sci. USA 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson, et al., Cell 37:767–778 at 777.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention.

Non-limiting examples of antigenic polypeptides or peptides that can be used to generate IL-19-specific antibodies include:a polypeptide comprising amino acid residues from about −5 to about 4 in SEQ ID NO:2; a polypeptide comprising amino acid residues from about 64 to about 82 in SEQ ID NO:2; and a polypeptide comprising amino acid residues from about 115 to about 125 in SEQ ID NO:2. As indicated above, the inventors have determined that the above polypeptide fragments are antigenic regions of the IL-19 protein.

The epitope-bearing peptides and polypeptides of the invention may be produced by any conventional means. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986).

As one of skill in the art will appreciate, IL-19 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric IL-19 protein or protein fragment alone (Fountoulakis et al., *J Biochem* 270:3958–3964 (1995)).

The entire disclosure of each document cited in this section on "Polypeptides and Peptides" is hereby incorporated herein by reference.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of an interleukin-19 protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verna et al., HUMAN CHROMOSOMES: A MANUAL OF BASIC TECHNIQUES, Pergamon Press, New York (1988).

Once a sequence has been mapped to a precise chromosomal location, the physical position of the sequence on the chromosome can be correlated with genetic map data. Such data are found, for example, in V. McKusick, MENDELIAN INHERITANCE IN MAN, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Treatment of Pathological Conditions by IL-19 Inhibition of Cytokine Production

As noted above, IL-19 is secreted by activated monocytes, and shares significant homology with human IL-10. Thus, it is believed by the inventors that IL-19 is active in inhibiting cytokine production during the mammalian immune response. The cytokines whose production may be affected by IL-19 include IFN-$\gamma$, TNF-$\alpha$, and IL-6.

One such activity of IL-19 is the ability to limit excessive production of gamma-interferon (IFN-$\gamma$), and hence the consequent effects of such production, including major histocompatibility (MHC) associated auto-immune diseases. As increased IFN-$\gamma$ expression has been implicated in an increase of MHC genes, which may then increase the chance of an autoimmune response against the MHC-overexpressing cells, the ability to limit IFN-$\gamma$ expression may be therapeutically valuable in the treatment of clinical manifestations of such MHC disorders. These include rheumatoid arthritis, systemic lupus erythematosus (SLE), myasthenia gravis, insulin-dependent diabetes mellilitus, and thyroiditis.

The down regulation of IFN-$\gamma$ by IL-19 may also be therapeutically valuable in treating parasitic infections such as leishmaniasis. Levels of IFN-$\gamma$, IL-2 and IL-4 are all involved in the regulation of the life cycle of this parasite. Thus, the ability to regulate the production of these cytokines by IL-19 will be therapeutically valuable.

Given the activities modulated by IL-19, it is readily apparent that a substantially altered (increased or decreased) level of expression of IL-19 in an individual compared to the standard or "normal" level produces pathological conditions such as those described above. It will also be appreciated by one of ordinary skill that, since the IL-19 protein of the invention is translated with a leader peptide suitable for secretion of the mature protein from the cells which express IL-19, when IL-19 protein (particularly the mature form) is added from an exogenous source to cells, tissues or the body of an individual, the protein will exert its modulating activities on any of its target cells. Therefore, it will be appreciated that conditions caused by a decrease in the standard or normal level of IL-19 activity in an individual, can be treated be administration of IL-19 protein. Thus, the invention further provides a method of treating an individual in need of an increased level of IL-19 activity comprising administering to such an individual a pharmaceutical composition comprising an amount of an isolated IL-19 polypeptide of the invention, particularly a mature form of the IL-19 protein of the invention, effective to increase the IL-19 activity level in such an individual.

One of ordinary skill will appreciate that effective amounts of the IL-19 polypeptides for treating an individual in need of an increased level of IL-19 activity can be determined empirically for each condition where administration of IL-19 is indicated. The polypeptide having IL-19 activity my be administered in pharmaceutical compositions in combination with one or more pharmaceutically acceptable excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition an other agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts.

For example, it is predicted that satisfactory results are obtained by oral administration of a polypeptide having IL-19 activity in dosages on the order of from 0.05 to 10 mg/kg/day, preferably 0.1 to 7.5 mg/kg/day, more preferably 0.1 to 2 mg/kg/day, administered once or, in divided doses, 2 to 4 times per day. On administration parenterally, for example by i.v. drip or infusion, dosages on the order of from 0.01 to 5 mg/kg/day, preferably 0.05 to 1.0 mg/kg/day and more preferably 0.1 to 1.0 mg/kg/day can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging may also be arranged in a patient specific manner to provide a predetermined concentration of an IL-19 activity in the blood, as determined by an RIA technique, for instance. Thus patient dosaging may be adjusted to achieve regular on-going trough blood levels, as measured by RIA, on the order of from 50 to 1000 ng/ml, preferably 150 to 500 ng/ml.

Pharmaceutical compositions of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the pharmaceutical composition, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f)—absorption accelerators such as quaternary ammonium compounds, g) wetting agents such as, for example, cetyl alcohol and glycerol monostearate, h)—absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isoptopyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar, and tragacanth, and mixtures thereof.

The active polypeptide can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the agent or inhibitor, stabilizers, preservatives, excipients, and the like. The preferred lipids are the phospholipids and the phosphatidyl cholates (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Use of IL-19 in Adoptive Immunotherapy of Cancer

Another therapeutic application of IL-19 is the administration of IL-19 in adoptive immunotherapy to prevent or reduce the production of cytokines believed to be responsible for many of the deleterious side effects currently encountered in adoptive immunotherapy. As used herein, "Adoptive immunotherapy" means therapy wherein functional cancer-fighting immune cells are transferred to a patient. The cancer-fighting immune cells preferably comprise tumor infiltrating lymphocytes (TILs) originating from the patient himself. As is known in the art, while IL-2 is useful in adoptive immunotherapy due to its ability to activate the killer cells transferred to the patent (Rosenberg et al., *Ann. Rev. Immunol.* 4: 681–709 (1988)), the severe side effects caused directly or indirectly by IL-2 have been an obstacle to the development of routine treatment protocols based on this approach (Hsu, D-H et al., WO 92/12726). As IL-19 is believed to be capable of preventing or reducing the production of cytokines responsible for these side effects, TILs cultured in the presence of both IL-2 and IL-19 prior to administration, wherein the administration of IL-2 and IL-19 is continued after the administration of those TILs to the patient, may reduce the deleterious side effects typical of adoptive immunotherapy.

Use of IL-19 Antagonists in the Restoration of Immunocompetency to T Helper Cells in HIV-Infected Patients Another therapeutic application of the IL-19 polypeptide of the invention is the use of the polypeptide to identify IL-19 antagonists, such as an antibody specific for binding to IL-19, which can then be used to increase the production of IL-2 in T helper cells. For example, patients infected with human immunodeficiency virus (HIV) have a decreased level of IL-2 production in non-virally infected T helper cells. IL-19 is believed to be capable of preventing or reducing the production of IL-2. Therefore, the administration of IL-19 antagonists may result in an increase in IL-2 production in HIV-infected patients. As IL-2 is responsible for T cell proliferation, the maintenance of IL-2 production is beneficial to HIV-infected patients.

Antagonists specific for IL-19 can be made by mutating the amino acid sequence of IL-19 using standard mutagenesis methods well known to those of ordinary skill in the art. Such methods include the use of M13 vectors to introduce single-site mutations, to delete random amino acids from IL-19, or to add amino acids. The resulting muteins are then tested in standard assays for the ability to compete with non-mutated IL-19, including assays which test the ability of the mutein, as compared with the IL-19 protein of the invention, to enhance IL-2 dependent proliferation of T cells in vitro.

Other suitable IL-19 antagonists include an antibody specific for binding to IL-19 (αIL-19) which interferes with its binding to the T helper receptor. Production of such antibodies has been described in full above.

The antibodies used in the method of the invention preferably are autologous for the patient, thereby minimizing further immunological problems. However, as immunodeficient individuals in need of this treatment will tend to be less reactive to non-self antibodies, non-self antibodies derived from cells of the same species will also be useful.

Having generally described the invention, the same will be more readily understood by reference to the following examples, which are provided by way of illustration and are not intended as limiting.

EXAMPLES

Example 1

Expression and Purification of IL-19 in *E. coli*

The DNA sequence encoding the mature IL-19 protein in the deposited cDNA clone was amplified using PCR oligonucleotide primers specific to the amino terminal sequences of the IL-19 protein and to vector sequences 3' to the gene. Additional nucleotides containing restriction sites to facilitate cloning were added to the 5' and 3' sequences respectively.

The 5' oligonucleotide primer had the sequence 5' GGC ATG CCA TGG AGTTAC AGT GTG TTT CCC 3 ' [SEQ ID NO:4] (sequences specific to the IL-19 nucleotide sequence are underlined), and included an NcoI restriction site.

The 3' primer had the sequence 5' GGA AGA TCT AGC TGA GGA CATTAC 3' [SEQ ID NO:5] containing the underlined 15 nucleotides complementary to the last 15 nucleotides immediately after the IL-19 protein coding sequence in FIG. 1. The 3' primer included a BglII restriction site.

The restriction sites were convenient to restriction enzyme sites in the bacterial expression vector pQE60, which were used for bacterial expression in these examples. (Qiagen, Inc. 9259 Eton Avenue, Chatsworth, Calif., 91311). pQE60 encodes ampicillin antibiotic resistance ("Amp") and contains a bacterial origin of replication ("ori"), an IPTG inducible promoter, a ribosome binding site ("RBS"), a 6-His tag and restriction enzyme sites. The amplified IL-19 protein DNA and the vector pQE60 both were digested with NcoI and BglII and the digested DNAs were then ligated together. Insertion of the IL-19 protein DNA into the restricted pQE60 vector placed the IL-19 protein coding region downstream of and operably linked to the vector's IPTG-inducible promoter and in-frame with an initiating ATG appropriately positioned for translation of IL-19 protein.

The ligation mixture was transformed into competent *E. coli* cells using standard procedures. Such procedures are described in Sambrook et al., MOLECULAR CLONING: A LABORATORY MANUAL, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan$^r$"), was used in carrying out the illustrative example described here. This strain, which is only one of many that are suitable for expressing IL-19 protein, is available commercially from Qiagen.

Transformants were identified by their ability to grow on LB plates in the presence of ampicillin and kanamycin. Plasmid DNA was isolated from resistant colonies and the identity of the cloned DNA was confirmed by restriction analysis.

Clones containing the desired constructs were grown overnight ("O/N") in liquid culture in LB media supplemented with both ampicillin (100 µg/ml) and kanamycin (25 µg/ml).

The O/N culture was used to inoculate a large culture, at a dilution of approximately 1:100 to 1:250. The cells were grown to an optical density at 600 nm ("OD600") of between 0.4 and 0.6. Isopropyl-B-D-thiogalactopyranoside ("IPTG") was then added to a final concentration of 0.1 mM to induce transcription from lac repressor sensitive promoters, by inactivating the lacI repressor. Cells subsequently were incubated further for 4 hours (FIG. 2 shows IL-19 protein induction; samples removed 0, 3, 5, 6, and 24 hours after the addition of IPTG were run on a 12.5% polyacrylamide gel and stained with brilliant blue). The mobility of the IL-19 protein is indicated by an arrow. Cells were then harvested by centrifugation and disrupted by gentle shaking overnight in 6M guanidine HCl in 50 mM NaPO$_4$ buffer at pH 8.0 at 4° C. The lysate was then centrifuged and passed over a Sepharose CL-4B (Pharmacia) column. The flowthrough was then passed over a column containing activated Ni$^{2+}$-NTA-agarose (Qiagen). IL-19 protein was collected from the column in a fraction consisting of 6M guanidine HCl pH 5.0. Guanidine HCl was removed from the IL-19-containing fraction by dialysis against successively reduced concentrations of guanidine in phosphate-buffered saline (PBS) at pH 5.5.

Example 2

Cloning and Expression of IL-19 in a Baculovirus Expression System

The cDNA sequence encoding the full length IL-19 protein in the deposited clone was amplified using PCR oligonucleotide primers corresponding to the 5' and 3' sequences of the gene:

The 5' primer had the sequence 5' GGC GGG ATC CCG CCA TCA TGA AGT TAC AGT GTG TTT CCC 3' [SEQ ID NO:6] containing the underlined BamHI restriction enzyme site followed by 29 bases of the sequence of IL-19 protein in FIG. 1. Inserted into an expression vector, as described below, the 5' end of the amplified fragment encoding IL-19 provided an efficient signal peptide. An efficient signal for initiation of translation in eukaryotic cells, as described by Kozak, M., J. Mol. Biol. 196:947–950 (1987) is appropriately located in the vector portion of the construct.

The 3' primer had the sequence 5'CCC AAG CTT GGT ACC TCA TCA AGC TGA GGA CAT TAC 3' [SEQ ID NO:7] containing the underlined Asp718 restriction site followed by nucleotides complementary to the last 21 nucleotides of the IL-19 coding sequence set out in FIG. 1.

The amplified fragment was isolated from a 1% agarose gel using a commercially available kit ("Geneclean," BIO 101 Inc., La Jolla, Calif.). The fragment then was digested with BamHI and Asp718 and again was purified on a 1% agarose gel. This fragment is designated herein F2.

The vector and pA2-GP were used to express the IL-19 protein in the baculovirus expression system, using standard methods, as described in Summers et al, A MANUAL OF METHODS FOR BACULOVIRUS VECTORS AND INSECT CELL CULTURE PROCEDURES, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites. The signal peptide of AcMNPV gp67, including the N-terminal methionine, is located just upstream of a BamHI site. The polyadenylation site of the simian virus 40 ("SV40") is used for efficient polyadenylation. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide. The IL-19 protein was also expressed in baculovirus using the pA2 vector.

Many other baculovirus vectors could be used in place of pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., Virology 170: 31–39, among others.

The plasmid was digested with the restriction enzymes BamHI and Asp718 and then was dephosphorylated using calf intestinal phosphatase, using routine procedures known in the art. The DNA was then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 were ligated together with T4 DNA ligase. *E. coli* HB101 cells were transformed with ligation mix and spread on culture plates. Bacteria were identified that contained the plasmid with the human IL-19 gene by digesting DNA from individual colonies using BamHI and Asp718 and then analyzing the digestion product by gel electrophoresis. The sequence of the cloned fragment was confirmed by DNA sequencing. This plasmid is designated herein pBacIL-19.

5 µg of the plasmid pBacIL-19 was co-transfected with 1.0 µg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84: 7413–7417 (1987). 1 µg of BaculoGold™ virus DNA and 5 µg of the plasmid pBacCKβ-15 were mixed in a sterile well of a microtiter plate containing 50 µl of serum-free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture was added drop-wise to Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation is continued at 27° C. for four days.

After four days the supernatant was collected and a plaque assay is performed, as described by Summers and Smith, cited above. An agarose gel with "Blue Gal" (Life Technologies Inc., Gaithersburg) was used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus was added to the cells. After appropriate incubation, blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus was used to infect Sf9 cells seeded in 35 mm dishes. Four days later the supernatants of these culture dishes were harvested and then they were stored at 4° C. A clone containing properly inserted hESSB I, II and III were identified by DNA analysis including restriction mapping and sequencing. This is designated herein as V-IL-19.

Sf9 cells were grown in Grace's medium supplemented with 10% heat-inactivated FBS. The cells were infected with the recombinant baculovirus V4L-19 at a multiplicity of infection ("MOI") of about 2 (about 1 to about 3). Six hours later the medium was removed and was replaced with SF900 II medium minus methionine and cysteine (available from Life Technologies Inc., Gaithersburg). 42 hours later, 5 µCi of $^{35}$S-methionine and 5 µCi $^{35}$S-cysteine (available from Amersham) were added. The cells were further incubated for 16 hours and then they were harvested by centrifugation, lysed and the labeled proteins were visualized by SDS-PAGE and autoradiography.

Example 3

In vitro Transcription/Translation of IL19 Protein

Recombinant IL-19 proteins were prepared using the TNT Coupled Wheat Germ Extract System (Promega, Madison, Wis.).

Figure 3:
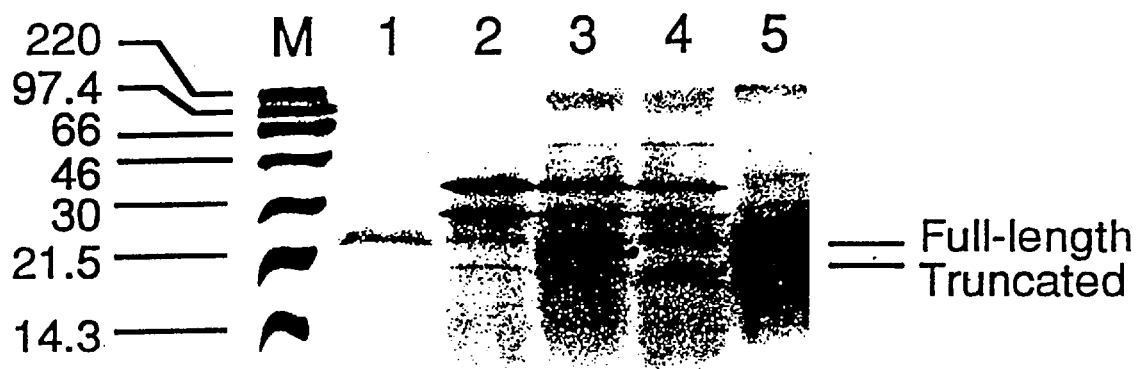
FIG. 3 is a protein gel showing full length and truncated IL-19 proteins produced in an in vitro coupled transcription/translation system (see Example 3).

25 µl of TNT wheat germ extract, 10 U T3 RNA polymerase, 1 mM amino acid mixture (methionine-free), 4 µCi $^{35}$S-methionine (1000 Ci/mmol), 40 U RNasin (Promega, Madison, Wis.), and 1 µg template DNA were combined in a final volume of 50 µl and incubated at 30° C. for 2 h. Coupled transcription/translation reactions included the following template DNAs: (1) No DNA, (2) pBluescript, (3) nucleotides 44–577 (corresponding to amino acids 1–177) of the IL-19 sequence shown in FIG. 1 cloned into pBluescript, (4) nucleotides 116–577 (corresponding to amino acids 25–177) OF THE IL-19 coding sequence cloned into pBluescript, (5) a gel-purified PCR product derived from the template described in (3) and amplified using M13 forward and reverse primers in a standard PCR reaction. Samples were heated to 95° C. for 10 minutes and a 5 µl aliquot of each sample was then loaded on to a 15% polyacrylamide gel. The gel was run at 100 volts for approximately 2 hours. The gel was then dried and exposed to X-ray film for 3 days at room temperature. The mobility of full-length and truncated (no signal sequence) IL-19 proteins are indicated in FIG. 3. An apparent molecular mass marker (M) shows the relative mobilities of 14.3, 21.5, 30, 46, 66, 97.4, and 220 kD proteins.

Example 4

Cloning and Expression in Mammalian Cells

Most of the vectors used for the transient expression of the IL-19 protein gene sequence in mammalian cells should carry the SV40 origin of replication. This allows the replication of the vector to high copy numbers in cells (e.g. COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of trancription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g. RSV, HTLVI, HIVI and the early promoter of the cytomegalovirus (CMV). However, cellular signals can also be used (e.g. human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 283,H9 and Jurkart cells, mouse NIH3T3 and C127 cells, Cos 1, Cos 7 and CV1, African green monkey cells, quail QC1–3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., *Biochem J.* 227.277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology,* 438–4470 (March, 1985)) plus a fragment of the CMV-enhancer (Boshart et al., *Cell* 41:521–530 (1985)). Multiple cloning sites, e.g. with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 4(a)

Cloning and Expression in COS Cells

The expression plasmid, pIL-19HA, is made by cloning a cDNA encoding IL-19 into the expression vector pcDNA4 (which can be obtained from Invitrogen, Inc.).

The expression vector pcDNA4 contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the IL-19 protein and an HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37: 767 (1984). The fusion of the HA tag to the target protein allows easy detection of the recombinant protein with an antibody that recognizes the HA epitope.

The plasmid construction strategy is as follows. The IL-19 cDNA of the deposited clone is amplified using primers that contain convenient restriction sites, much as described above regarding the construction of expression vectors for expression of IL-19 in *E. coli*. To facilitate detection, purification and characterization of the expressed IL-19, one of the primers contains a hemagglutinin tag ("HA tag") as described above.

Suitable primers include the following, which are used in this example. The 5' primer, containing the underlined BamHI site, an AUG start codon and 22 bp of the 5' coding region has the following sequence:

5' GGC GGG ATC CCG CCA TGA AGT TAC AGT GTG TTT CCC 3' (SEQ ID NO:8).

The 3' primer, containing the underlined Asp 718 site, a stop codon, 10 codons thereafter forming the hemagglutinin HA tag, and 25 bp of 3' coding sequence (at the 3' end) has the following sequence:

5' CCC AAG CTT GGT ACC TCA TCA GAA AGC GTA GTC TGG GAC GTC GTA TGG GTA AGC TGA GGA CAT TAC TTC ATG ATT C 3' (SEQ ID NO:9).

The PCR amplified DNA fragment and the vector, pcDNAI/Amp, are digested with HindIII and XhoI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis and gel sizing for the presence of the IL-19-encoding fragment.

For expression of recombinant IL-19, COS cells are transfected with an expression vector, as described above, using DEAE-DEXTRAN, as described, for instance, in Sambrook et al., MOLECULAR CLONING: A LABORATORY MANUAL, Cold Spring Laboratory Press, Cold Spring Harbor, N.Y. (1989). Cells are incubated under conditions for expression of IL-19 by the vector.

Expression of the IL-19/HA fusion protein is detected by radiolabelling and immunoprecipitation, using methods described in, for example Harlow et al., ANTIBODIES: A LABORATORY MANUAL, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 4(b)

Cloning and Expression in CHO Cells

The vector pC4 is used for the expression of IL-19 protein. Plasmid pC4 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370,Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC4 contains for the expression of the gene of interest a strong promoter of the long terminal repeat (LTR) of the Rouse Sarcoma Virus (Cullen, et al., Molecular and Cellular Biology, March 1985:438–4470) plus a fragment isolated from the enhancer of the immediate early gene of human cytomegalovirus (CMV) (Boshart et al., Cell 41:521–530, 1985). Downstream of the promoter are the following single restriction enzyme cleavage sites that allow the integration of the genes: BamHI, PvuII, and NruI. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzyme BaniHI and then dephosphorylated using calf intestinal phosphates by procedures known in the art. The vector is then isolated from a 1% agarose gel.

The DNA sequence encoding IL-19 protein is amplified using PCR oligonucleotide primers specific to the amino terminal sequence of the IL-19 protein and to carboxy terminal sequence 3' to the gene. Additional nucleotides containing restriction sites to facilitate cloning are added to the 5' and 3' sequences respectively.

The 5' primer has the sequence 5' GGC GGG ATC CCG CCA TCA TGA AGT TAC AGT GTG TTT CCC 3' (SEQ ID NO: 10), containing the underlined BamHI restriction enzyme site followed by Kozak sequence and 23 bases of the sequence of IL-19 in FIG. 1. The 3' primer has the sequence 5' CCC AAG CTT GGT ACC TCA TCA AGC TGA GGA CAT TAC 3' (SEQ ID NO: 11), containing the underlined Asp 718 restriction site followed by nucleotides complementary to 15 bp of the nucleotide sequence preceding the stop codon in FIG. 1. The restrictions sites are convenient to restriction enzyme sites in the CHO expression vector pC4.

The amplified fragments are isolated from a 1% agarose gel as described above and then digested with the endonucleases BamHI and Asp718 and then purified again on a 1% agarose gel.

The isolated fragment and the dephosphorylated vector are then ligated with T4 DNA ligase. *E. coli* HBO101 cells are then transformed and bacteria identified that contained the plasmid pC4 inserted in the correct orientation using the restriction enzyme BamHI. The sequence of the inserted gene is confirmed by DNA sequencing.

Transfection of CHO-DHFR-cells

Chinese hamster ovary cells lacking an active DHFR enzyme are used for transfection. 5 $\mu$g of the expression plasmid pC4 are cotransfected with 0.5 $\mu$g of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25 nM, 50 nM, 100 nM, 200 nM, 400 nM, 800 nM). Clones growing at the highest concentrations of methotrexate are then transferred to new 6-well plates containing even higher concentrations of methotrexate (1 $\mu$M, 2 $\mu$M, 5 $\mu$M, 10 mM, 20 mM). The same procedure is repeated until clones grow at a concentration of 100 $\mu$M-200 $\mu$M.

The expression of the desired gene product is analyzed by Western blot analysis and SDS-PAGE or by reverse phase HPLC analysis.

Example 5

Tissue Distribution of IL-19 Protein Expression

Northern blot analysis was carried out to examine the levels of expression of IL-19 protein in human tissues, using methods described by, among others, Sambrook et al, cited above.

Figure 4:
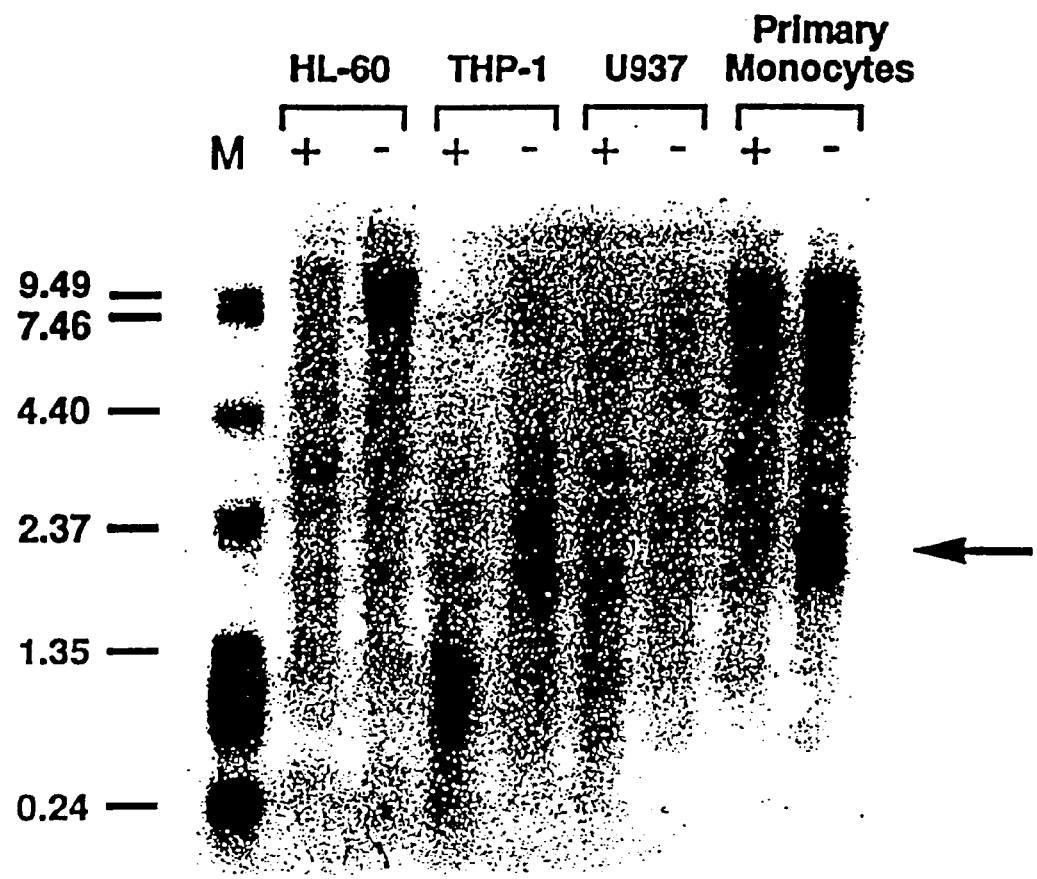
FIG. 4 is a northern blot analysis of IL-19 expression in human tissue (HL-60, THP-1, U937 and primary human monocytes) (see Example 5).
Figure 6:
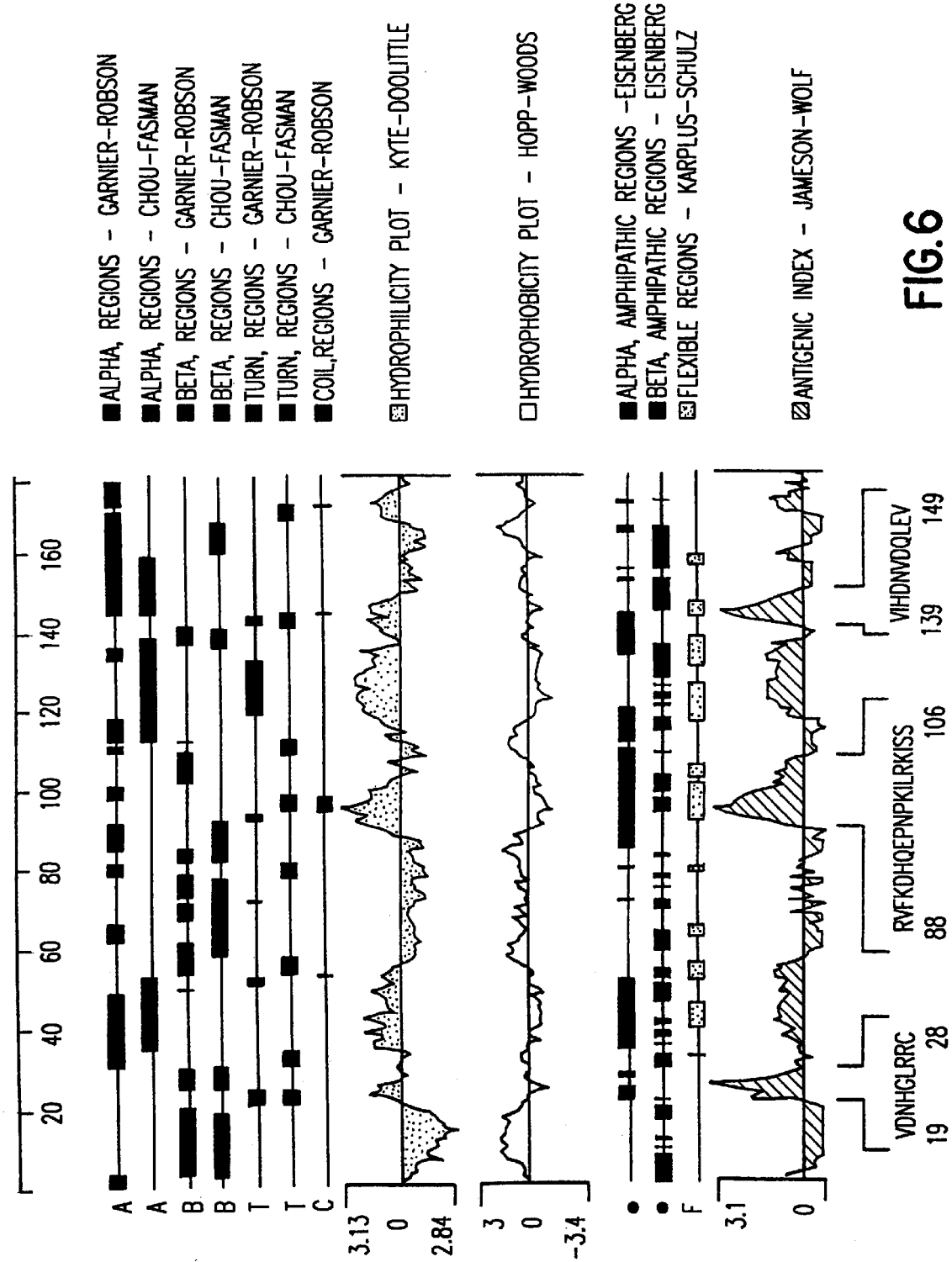
FIG. 6 shows an analysis of the IL-19 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues about 19 to about 28, about 88 to about 106, and about 139 to about 149 in FIG. 1 correspond to the shown highly antigenic regions of the IL-19 protein. These highly antigenic fragments in FIG. 1 correspond to the following fragments, respectively, in SEQ ID NO:2: amino acid residues about −5 to about 4, about 64 to about 82, and about 115 to about 125.

HL-60, THP-1 and U937 cell lines and primary human monocytes isolated by adherence from a mixed leukocyte population were grown for 12 hours either in the presence (+) or absence (−) of bacterial lipopolysaccharide (LPS). Total RNA was prepared from the cultures with TRIzol Reagent (Life Technologies, Gaithersburg, Md.) essentially as described by the manufacturer. Total RNA (10 $\mu$g) was dried completely, resuspended in a formamide/formaldehyde loading buffer, and resolved by electrophoresis through a 1% agarose gel containing 2.2 M formaldehyde. The gel was transferred overnight in 20× SSC to a nylon membrane (Boehringer Mannheim, Indianapolis, Ind.). Probe DNA was prepared by PCR amplifying the entire IL-19 insert shown in FIG. 1 using M13 Forward and Reverse primers. Probe DNA (25 ng) was labeled with 32P using the RediPrime Random Primer Labeling Kit (Amersham Life Science) to a specific activity of greater than $10^6$ CPM/ng. The blot was hybridized with denatured probe in a 10 ml Hybrizol hybridization solution overnight at 42° C. The blot was then washed in approximately 100 ml of 0.2× SSC/0.1% SDS at 25° C. for 20 minutes, and then twice in approximately 100 ml of 0.2× SSC/0.1% SDS at 65° C. for 15 min. The blot was then exposed to x-ray film for 5 days, and is shown in FIG. 4. The arrow shows the migration of the IL-19-specific RNA. An RNA marker shows the relative mobilities of 0.24, 1.35, 2.37, 4.40, 7.46, and 9.49 kb RNAs.

It will be clear that the invention may be practiced otherwise than as particularly described in the foregoing description and examples.

Numerous modifications and variations of the present invention are possible in light of the above teachings and, therefore, are within the scope of the appended claims.

The disclosures of all patents, patent applications, and publications referred to herein are hereby incorporated by reference.

What is claimed is:

1. An isolated protein comprising amino acids 1 to 153 of SEQ ID NO:2.

2. The protein of claim 1, comprising amino acids −23 to 153 of SEQ ID NO:2.

3. The protein of claim 2, comprising amino acids −24 to 153 of SEQ ID NO:2.

4. The protein of claim 1, which is produced by a recombinant host cell.

5. The protein of claim 1, which further comprises a heterologous protein.

6. The protein of claim 5, wherein said heterologous protein comprises Fc.

7. The protein of claim 1, which is glycosylated.

8. A composition comprising the protein of claim 1, and a pharmaceutically acceptable carrier.

9. An isolated protein produced by a method comprising (a) expressing the protein of claim 1 in a cell, and (b) recovering said protein.

10. An isolated protein comprising the mature amino acid sequence encoded by the cDNA in ATCC Deposit No. 97662.

11. The protein of claim 10, comprising the full length amino acid sequence encoded by the cDNA in ATCC Deposit No. 97662.

12. The protein of claim 10, which is produced by a recombinant host cell.

13. The protein of claim 10, which further comprises a heterologous protein.

14. The protein of claim 13, wherein said heterologous protein comprises Fc.

15. The protein of claim 10, which is glycosylated.

16. A composition comprising the protein of claim 10, and a pharmaceutically acceptable carrier.

17. An isolated protein produced by a method comprising (a) expressing the protein of claim 10 in a cell, and (b) recovering said protein.

18. An isolated first protein at least 95% identical to a second protein consisting of amino acids 1 to 153 of SEQ ID NO:2, wherein said first protein inhibits the synthesis of at least one cytokine selected from the group consisting of: interferon-γ, lymphotoxin, IL-2, IL-3 and GM-CSF.

19. The first protein of claim 18 at least 95% identical to a second protein consisting of amino acids −23 to 153 of SEQ ID NO:2.

20. The first protein of claim 19 at least 95% identical to a second protein consisting of amino acids −24 to 153 of SEQ ID NO:2.

21. The protein of claim 18, which is produced by a recombinant host cell.

22. The protein of claim 18, which is fused to a heterologous protein.

23. The protein of claim 18, which is fused to Fc.

24. The protein of claim 18, which is glycosylated.

25. A composition comprising the protein of claim 18, and a pharmaceutically acceptable carrier.

26. An isolated protein produced by a method comprising (a) expressing the protein of claim 18 in a cell, and (b) recovering said protein.

27. An isolated first protein at least 95% identical to a second protein consisting of the mature amino acid sequence encoded by the cDNA in ATCC Deposit No. 97662, wherein said first protein inhibits the synthesis of at least one cytokine selected from the group consisting of: interferon-γ, lymphotoxin, IL-2, IL-3 and GM-CSF.

28. The first protein of claim 27 at least 95% identical to a second protein consisting of the full length amino acid sequence encoded by the cDNA in ATCC Deposit No. 97662.

29. The protein of claim 27, which is produced by a recombinant host cell.

30. The protein of claim 27, which is fused to a heterologous protein.

31. The protein of claim 27, which is fused to Fc.

32. The protein of claim 27, which is glycosylated.

33. A composition comprising the protein of claim 27 and a pharmaceutically acceptable carrier.

34. An isolated protein produced by a method comprising (a) expressing the protein of claim 27 in a cell, and (b) recovering said protein.

35. An isolated protein consisting of at least 30 contiguous amino acids of SEQ ID NO:2.

36. The protein of claim 35 consisting of at least 50 contiguous amino acids of SEQ ID NO:2.

37. The protein of claim 35, which is produced by a recombinant host cell.

38. The protein of claim 35, which is fused to a heterologous protein.

39. The protein of claim 35, which is fused to Fc.

40. The protein of claim 35, which is glycosylated.

41. A composition comprising the protein of claim 35 and a pharmaceutically acceptable carrier.

42. An isolated protein produced by a method comprising (a) expressing the protein of claim 35 in a cell, and (b) recovering said protein.

43. An isolated protein consisting of at least 30 contiguous amino acids of the full length amino acid sequence encoded by the cDNA in ATCC Deposit No. 97662.

44. The protein of claim 43 consisting of at least 50 contiguous amino acids of the full length amino acid sequence encoded by the cDNA in ATCC Deposit No. 97662.

45. The protein of claim 43, which is produced by a recombinant host cell.

46. The protein of claim 43, which is fused to a heterologous protein.

47. The protein of claim 43, which is fused to Fc.

48. The protein of claim 43, which is glycosylated.

49. A composition comprising the protein of claim 43 and a pharmaceutically acceptable carrier.

50. An isolated protein produced by a method comprising (a) expressing the protein of claim 43 in a cell, and (b) recovering said protein.

51. An isolated protein consisting of a fragment of the amino acid sequence of SEQ ID NO:2, wherein said fragment inhibits the synthesis of at least one cytokine selected from the group consisting of: interferon-γ, lymphotoxin, IL-2, IL-3 and GM-CSF.

52. The protein of claim 51, which is produced by a recombinant host cell.

53. The protein of claim 51, which is fused to a heterologous protein.

54. The protein of claim 51, which is fused to Fc.

55. The protein of claim 51, which is glycosylated.

56. A composition comprising the protein of claim 51 and a pharmaceutically acceptable carrier.

57. An isolated protein produced by a method comprising (a) expressing the protein of claim 51 in a cell, and (b) recovering said protein.

58. An isolated protein consisting of a fragment of the complete amino acid sequence encoded by the cDNA in ATCC Deposit No. 97662, wherein said fragment inhibits the synthesis of at least one cytokine selected from the group consisting of: interferon-γ, lymphotoxin, IL-2, IL-3 and GM-CSF.

59. The protein of claim 58, which is produced by a recombinant host cell.

60. The protein of claim 58, which is fused to a heterologous protein.

61. The protein of claim 58, which is fused to Fc.

62. The protein of claim 58, which is glycosylated.

63. A composition comprising the protein of claim 58 and a pharmaceutically acceptable carrier.

64. An isolated protein produced by a method comprising (a) expressing the protein of claim 58 in a cell, and (b) recovering said protein.

* * * * *

UNITED STATES PATENT AND TRADEMARK OFFICE
CERTIFICATE OF CORRECTION

PATENT NO. : 6,583,270 B2
DATED : June 24, 2003
INVENTOR(S) : Rosen et al.

It is certified that error appears in the above-identified patent and that said Letters Patent is hereby corrected as shown below:

<u>Title page,</u>
Item [54], please correct the title to read -- INTERLEUKIN-19 POLYPEPTIDES AND VARIANTS THEREOF --

Signed and Sealed this

Eleventh Day of May, 2004

JON W. DUDAS
*Acting Director of the United States Patent and Trademark Office*

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 966 base pairs
      (B) TYPE: nucleic acid (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 44..574

(ix) FEATURE:
        (A) NAME/KEY: sig_peptide
        (B) LOCATION: 44..115

(ix) FEATURE:
        (A) NAME/KEY: mat_peptide
        (B) LOCATION: 116..574

(xi) SEQUENCE DESCRIPTION: SEQ ID NO:1:

```
GGCACGAGCA CAAGGAGCAG CCCGCAAGCA CCAAGTGAGA GGC ATG AAG TTA CAG        55
                                              Met Lys Leu Gln
                                              -24

TGT GTT TCC CTT TGG CTC CTG GGT ACA ATA CTG ATA TTG TGC TCA GTA       103
Cys Val Ser Leu Trp Leu Leu Gly Thr Ile Leu Ile Leu Cys Ser Val
-20             -15                 -10                     -5

GAC AAC CAC GGT CTC AGG AGA TGT CTG ATT TCC ACA GAC ATG CAC CAT       151
Asp Asn His Gly Leu Arg Arg Cys Leu Ile Ser Thr Asp Met His His
                1               5                   10

ATA GAA GAG AGT TTC CAA GAA ATC AAA AGA GCC ATC CAA GCT AAG GAC       199
Ile Glu Glu Ser Phe Gln Glu Ile Lys Arg Ala Ile Gln Ala Lys Asp
        15                  20                  25

ACC TTC CCA AAT GTC ACT ATC CTG TCC ACA TTG GAG ACT CTG CAG ATC       247
Thr Phe Pro Asn Val Thr Ile Leu Ser Thr Leu Glu Thr Leu Gln Ile
        30                  35                  40

ATT AAG CCC TTA GAT GTG TGC TGC GTG ACC AAG AAC CTC CTG GCG TTC       295
Ile Lys Pro Leu Asp Val Cys Cys Val Thr Lys Asn Leu Leu Ala Phe
        45                  50                  55              60

TAC GTG GAC AGG GTG TTC AAG GAT CAT CAG GAG CCA AAC CCC AAA ATC       343
Tyr Val Asp Arg Val Phe Lys Asp His Gln Glu Pro Asn Pro Lys Ile
                65                  70                  75

TTG AGA AAA ATC AGC AGC ATT GCC AAC TCT TTC CTC TAC ATG CAG AAA       391
Leu Arg Lys Ile Ser Ser Ile Ala Asn Ser Phe Leu Tyr Met Gln Lys
                80                  85                  90

ACT CTG CGG CAA TGT CAG GAA CAG AGG CAG TGT CAC TGC AGG CAG GAA       439
Thr Leu Arg Gln Cys Gln Glu Gln Arg Gln Cys His Cys Arg Gln Glu
                95                  100                 105

GCC ACC AAT GCC ACC AGA GTC ATC CAT GAC AAC TAT GAT CAG CTG GAG       487
Ala Thr Asn Ala Thr Arg Val Ile His Asp Asn Tyr Asp Gln Leu Glu
        110                 115                 120

GTC CAC GCT GCT GCC ATT AAA TCC CTG GGA GAG CTC GAC GTC TTT CTA       535
Val His Ala Ala Ala Ile Lys Ser Leu Gly Glu Leu Asp Val Phe Leu
125             130                 135                     140

GCC TGG ATT AAT AAG AAT CAT GAA GTA ATG TCC TCA GCT TGATGACAAG        584
Ala Trp Ile Asn Lys Asn His Glu Val Met Ser Ser Ala
                145                 150

GAACCTGTAT AGTGATCCAG GGATGAACAC CCCCTGTGCG GTTTACTGTG GGAGACAGCC     644

CACCTTGAAG GGGAAGGAGA TGGGGAAGGC CCCTTGCAGC TGAAAGTCCC ACTGGCTGGC     704

CTCAGGCTGT CTTATTCCGC TTGAAAATAG CCAAAAAGTC TACTGTGGTA TTTGTAATAA     764

ACTCTATCTG CTGAAAGGGC CTGCAGGCCA TCCTGGGAGT AAAGGGCTGC CTTCCCATCT     824

AATTTATTGT GAAGTCATAT AGTCCATGTC TGTGATGTGA GCCAAGTGAT ATCCTGTAGT     884

ACACATTGTA CTGAGTGGTT TTTCTGAATA AATTCCATAT TTTACCTATG GAAAAAAAA     944
```

AAAAAAAAAA AAAAAAAAA AA                                                    966

(2) INFORMATION FOR SEQ ID NO:2:

(i) SEQUENCE CHARACTERISTICS:
        (A) LENGTH: 177 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Leu Gln Cys Val Ser Leu Trp Leu Leu Gly Thr Ile Leu Ile
-24             -20             -15             -10

Leu Cys Ser Val Asp Asn His Gly Leu Arg Arg Cys Leu Ile Ser Thr
            -5                   1               5

Asp Met His His Ile Glu Glu Ser Phe Gln Glu Ile Lys Arg Ala Ile
        10              15                  20

Gln Ala Lys Asp Thr Phe Pro Asn Val Thr Ile Leu Ser Thr Leu Glu
25              30                  35                  40

Thr Leu Gln Ile Ile Lys Pro Leu Asp Val Cys Cys Val Thr Lys Asn
                45              50                  55

Leu Leu Ala Phe Tyr Val Asp Arg Val Phe Lys Asp His Gln Glu Pro
                60              65                  70

Asn Pro Lys Ile Leu Arg Lys Ile Ser Ser Ile Ala Asn Ser Phe Leu
            75              80              85

Tyr Met Gln Lys Thr Leu Arg Gln Cys Gln Glu Gln Arg Gln Cys His
            90              95                  100

Cys Arg Gln Glu Ala Thr Asn Ala Thr Arg Val Ile His Asp Asn Tyr
105             110                 115                 120

Asp Gln Leu Glu Val His Ala Ala Ala Ile Lys Ser Leu Gly Glu Leu
                125             130                 135

Asp Val Phe Leu Ala Trp Ile Asn Lys Asn His Glu Val Met Ser Ser
            140             145                 150

Ala (2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

ACCTGAGGTC TGATGGCAAA GTCCAAGAAT                                            30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GGCATGCCAT GGAGTTACAG TGTGTTTCCC                                            30

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GGAAGATCTA GCTGAGGACA TTAC                                              24
```

(2) INFORMATION FOR SEQ ID NO:6:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
GGCGGGATCC CGCCATCATG AAGTTACAGT GTGTTTCCC                               39
```

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
CCCAAGCTTG GTACCTCATC AAGCTGAGGA CATTAC                                  36
```

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
GGCGGGATCC CGCCATGAAG TTACAGTGTG TTTCCC                                  36
```

(2) INFORMATION FOR SEQ ID NO:9:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
CCCAAGCTTG GTACCTCATC AGAAAGCGTA GTCTGGGACG TCGTATGGGT AAGCTGAGGA        60

CATTACTTCA TGATT                                                        75
```

(2) INFORMATION FOR SEQ ID NO:10:

(i) SEQUENCE CHARACTERISTICS:
    (A) LENGTH: 39 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:10:

GGCGGGATCC CGCCATCATG AAGTTACAGT GTGTTTCCC                        39

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CCCAAGCTTG GTACCTCATC AAGCTGAGGA CATTAC                           36

(2) INFORMATION FOR SEQ ID NO:12:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ATAGGTAAAA TATGGAATTT ATTCAGAAAA ACCACTCAGT ACAATGTGTA CTACAGGATA      60

TCACTTGGCT CACATCACAG ACATGGACTA TATGACTTCA CAATAAATTA GACGGGAAGG    120

CAGCCCTTTA CTCCCAGGAT GGCCTGCAGG CCTTTCAGCA GATAGAGTTT ATTACAAATA    180

CCACAGTAGA CTTTTTGGCT ATTTTCAAGC GGAATAAGAC AGCCTGAGGC CAGCCAGTGG    240

GACTTTCAGC TGCCNGGGGC CTTCCCCATC TCCTTCCCCT TCAAGGTGGG CTGTCTCCCA    300

CAGTAAACCG CACANGGGGT GTTCATCCCT GGATCACTAT ACAGGTTCCT TGTCATCAAG    360

CTGAGGACAT TACTTCATGA TTCTTATTAA TCCAGGCTAG AAAGACGTCG AGCTCTCCCA    420

GGGATTTAAT GGCAGCAGCG TGGACCTCCA GCTGATCATA GTTGTCATGG ATGACTCTGG    480

TGGCATTGGT GGCTTCTGNC TGCAGTGACA ATGCCTCTGT TCTGACATTG CGCAGAGTTT    540

TCTGCATGTA GANGAAGAGT TGGCAATGNG CTGATTTTCT CAAGATTT               588

(2) INFORMATION FOR SEQ ID NO:13:

(i) SEQUENCE CHARACTERISTICS:
        (A) LENGTH: 514 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

ANAGGTAAAA TATGGAATTT ATTCAGAAAA ACCACTCAGT ACAATGTGTA CTACAGGATA      60

TCACTTGGCT CACATCACAG ACATGGACTA TATGACTTCA CAATAAATTA GANGGGAAGG    120

CAGCCCTTTA CTCCCAGGAT GGCCTGCAGG CCTTTCAGCA GATAGAGTTT ATTACAAATA    180

```
CCACAGTAGA CTTTTTGGCT ACCTTCAAGC GGAATAAGAC AGCCTGAGGC CAGCCAGTGG      240

GACTTTCAGC TGCCNGGGGC CTTCCCCATC TCCTTCCCCT TCAAGGTGGG CTGTCTCCCA      300

CAGTAAACCG CACNCGGGGT GTTCATCCCT GGATCACTAT ACAGGTTCCT TGTCATCAAG      360

CTGAGGACAT TACTTCATGA TTCTTATTAA TCCAGGCTAG AAAGACGTCG AGCTCTCCCA      420

GGGATTTAAT GGCAGCAGCG TGGAACTCCA GCTGATCATA GTTGTCATGG ATGACNCTGG      480

TGGNTTGGTG GCTTCCGGCT GCAGTGACAT GCCT                                 514
```

(2) INFORMATION FOR SEQ ID NO:14:

(i) SEQUENCE CHARACTERISTICS:
        (A) LENGTH: 574 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

```
ACCCCAAAAT CTTGAGAAAA ATCAGCAGCA TTGCCGNCGN GTNNGGGGGT GNGGGGGAGG       60

NGNNGAGNNG NNCNCTNTAA GAGNCCNCNN AAANGNGTTG GGACCAATGC CACCAGAGTC      120

ATCCATGACA ACTATGATCA GCTGGAGGTC CACGCTGCTG CCATTAAATC CCTGGGAGAG      180

CTCGACGTCT TTCTAGCCTG GATTAATANG AAGNATGGAG GNNGGTGNGN NGCGGGGTTG      240

TGAGGNNGCT GGGANGNGGN GCTGGGTNNG GAGTNGNNGT TGCCGCGNNT NGGGGAGNNA      300

GTGCANCCTG AAGGGGAAGG AGATGGGGAA GGCCCCTTGC AGCTGAAAGT CCCACTGGCT      360

GGCCTCAGGC TGTCTTATTC CGCTTGAAAA TAGCCAAAAA GTCTACTGTG GTATTTGTAA      420

TAAACTCTAT CTGCTGAAAG GGCCTGCAGC AATCCTGGGA GTAAGGGCTG CCTTCCCANC      480

TAATTTATTG TGAAGTCATA TAGTCCATGT CTGTGATGTG AGCCAAGTGA TATCTGTAGT      540

ACACATTGTA CTGAGTGGTT TTCTGAATAA TTCA                                 574
```

(2) INFORMATION FOR SEQ ID NO:15:

(i) SEQUENCE CHARACTERISTICS:
        (A) LENGTH: 594 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
CACCCCAAAA TCTTGAGAAA AATCAGCAGC ATTGCCAGNN CGNGGCNGGN CCGTGNGCNN       60

GNNGNNGNNN NCNGGNNGCN CNCNTTAAAA AGCCNNNNNN ANGGGTTCNG GGACCCAAT       120

GCCACCAGAG TCATCCATGA CAACTATGAT CAGCTGGAGG TCCACGCTGC TGCCATTAAA      180

TCCCTGGGAG AGCTCGACGT CTTTCTAGCC TGGATTAATA AGAAGCAGGG NGGGNGGCGG      240

NGNGGGCGTN CCGTGNNCGG GNNAGGGGNG GGNCGGTGNG NNNGCGCGNC GNGGTGGANN      300

NGGTNGCGGN GGNNGCGCTG GGGANGTGNT NGGAAGGGCC CTGCAGCTGA AAGTCCCACT      360

GGCTGGCCTC AGGTGTCTTA TTCCGCTTGA AAATAGCCAA AAAGTCTACT GTGGTATTTG      420

TAATAAACTC TATCTGCTGA AAGGGCCTGC AGCATTCCTG GGAGTAAAGG CTGCCTTCC       480

CATCTAATTT ATTGTGAAGT CATATAGTCC ATGTCTGTGA TGTGAGCCAA GTGATATCCT      540

GTAGTACACA TTGTACTGAG TGGTTTTTCT GAATAAATTC ATATTTACCT TAAA            594
```

(2) INFORMATION FOR SEQ ID NO:16:

(i) SEQUENCE CHARACTERISTICS:
        (A) LENGTH: 270 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
GCACTACTTC CAGAACACAC AAGGCCTGAT CTTCGTGGTG GACAGCAATG ACAGAGAGCG        60

TGTGAACGAG GCCCGTNAGG AGCTCATGAG GATGCTGGCC GAGGACGAGN TCCGGGATGC       120

TGTCCTCCTG GTGTTCGCCA ACAAGCAGGA CCTCCCCAAC GNCATGAATG CGGCCGAGAT       180

CACAGACAAG CTGGGGCTGC ACTCACTACG CCACAGGAAC TGGTACATTC AGGCCACCTN       240

CGNCACCAGC GGCGACGGGC TCTATGAAGG                                        270
```